United States Patent
Nonaka et al.

[11] Patent Number: 5,834,661
[45] Date of Patent: Nov. 10, 1998

[54] METHOD OF DETECTING DEFECTS IN MATERIALS USING INFRARED THERMOGRAPHY

[75] Inventors: Katsunobu Nonaka, Tsuchiura; Makoto Tanaka, Tsukuba; Kazuyoshi Sekine, Yokohama, all of Japan

[73] Assignee: Agency of Industrial Science & Technology, Ministry of International Trade & Industry, Tokyo, Japan

[21] Appl. No.: 747,925

[22] Filed: Nov. 12, 1996

[30] Foreign Application Priority Data

Nov. 15, 1995 [JP] Japan ................................. 7-321099

[51] Int. Cl.[6] .................................................. G01N 25/72
[52] U.S. Cl. ................................................. 073/866; 374/5
[58] Field of Search .................................. 374/5, 45, 124, 374/129, 137, 57; 73/866; 250/341.6, 330

[56] References Cited

U.S. PATENT DOCUMENTS

| 5,144,149 | 9/1992 | Frosch | 250/330 |
| 5,292,195 | 3/1994 | Crisman, Jr. | 250/330 |
| 5,505,543 | 4/1996 | Webbeking | 374/129 |

*Primary Examiner*—Christine K. Oda
*Attorney, Agent, or Firm*—Oblon, Spivak, McClelland, Maier & Neustadt, P.C.

[57] ABSTRACT

A method of detecting defects in materials using infrared thermography, includes placing the rear surface of an object to be inspected close to the front surface of a thermoplate controlled by a temperature controller, and the front surface of the object in a vacuum chamber. At the other end of the vacuum chamber, on the outside, an infrared camera is arranged facing the object, so that a vacuum is maintained between the object and the camera. Defects are detected from thermal images of the object, obtained with the infrared camera.

3 Claims, 4 Drawing Sheets

METHOD OF DETECTING DEFECTS IN MATERIALS USING INFRARED THERMOGRAPHY

BACKGROUND OF THE INVENTION

1. Field of the Invention

This invention relates to a method of detecting defects in materials by infrared thermography, utilizing thermoelectricity.

2. Description of the Prior Art

Conventional methods of detecting defects in materials include the acoustic emission method, the ultrasound method and the magnetic flaw detection method. These methods are limited by the fact that they use sensors that have to be brought near or into contact with the object to be inspected. Inspection by remote sensing infrared thermography is a powerful, non-contact, non-destructive inspection technology that uses high-resolution, high-precision infrared detectors to detect flaws, blemishes, voids and other surface and internal defects in materials.

A suitable thermal field has to be applied by some kind of method to an object that is to be inspected for defects using infrared thermography. Various methods of applying a thermal field for this purpose have been developed and reports published relating to the efficacy of the methods. In one method, a heater or the like is used to heat or cool the front or back surface of the object, while in another method, a stream of hot or cool air is directed toward the object from the direction of an infrared camera, and this is followed by natural cooling or forced cooling by a blower, and the resultant surface temperature distribution is used to detect the presence of any defects.

However, these methods of applying a thermal field all have drawbacks. Specifically, the way of applying a thermal field and the surrounding temperature have a major influence on the temperature distribution on the surface of an object, and a lack of uniform temperature caused by temperature fluctuations can make detection of microscopic defects very difficult.

An object of the present invention is to provide a method of detecting defects in materials using infrared thermography, in which the surface state of an examination object is protected from external disturbance while the thermal field is being applied to an object and provides a thermal field that maintains good thermal image reproducibility.

A further object of the present invention is to provide a method of detecting defects in materials using infrared thermography, in which cooling and heating of a sample can be controlled with good precision, a desired set heat cycle can be applied to the sample and microscopic defects can be detected effectively.

SUMMARY OF THE INVENTION

In accordance with the present invention, the above object is attained by a method of detecting defects in materials using infrared thermography, comprising:

placing a rear surface of an examination object close to a front surface of a thermoelectric plate (thermoplate) controlled by a temperature controller;

positioning a front surface of the examination object in a vacuum chamber;

disposing an infrared camera outside the vacuum chamber facing the examination object and maintaining a vacuum between the examination object and the infrared camera; and detecting defects in the object from thermal images obtained by the infrared camera.

Thus, as described above, a thermal field can be applied to an object to be examined with good reproducibility by eliminating disturbances from the outside air by heating and cooling the object in a vacuum chamber.

In the above defect detection method, when the surface of the examination object is coated with a heat-resistant paint, detailed thermal images are used to detect defects, and the thermal images can be clarified by using an infrared camera to obtain thermal images of the object under different conditions and using image subtraction processing.

Further features of the invention, its nature and various advantages will be more apparent from the accompanying drawings and following detailed description of the invention.

BRIEF DESCRIPTION OF THE DRAWINGS

FIG. 3 (B) is a photograph showing a thermogram of the sample "A" structure with a small void, obtained while them sample was being heated in the air;

FIG. 8 (B) is a drawing showing the presence of voids in the same sample as FIG. 8 (A), confirmed by using soft X-rays; and FIG. 8 (C) is a side view of the sample shown in FIG. 8 (B).

DESCRIPTION OF THE PREFERRED EMBODIMENT

Figure 1:
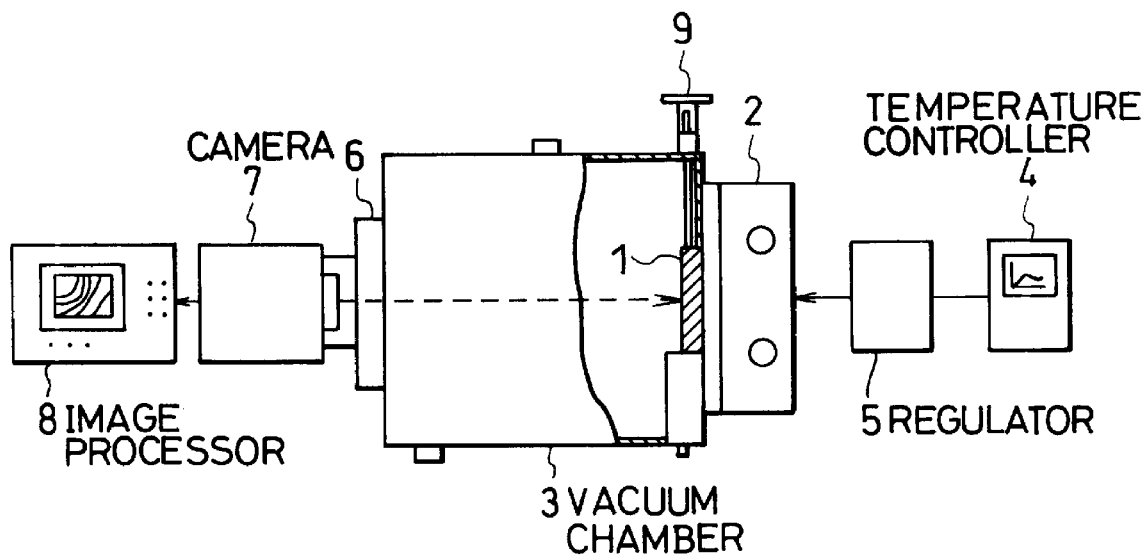
FIG. 1 is a block diagram showing a configuration of an embodiment of the method of detecting defects in materials using infrared thermography according to the present invention.

FIG. 1 shows a configuration of an apparatus for detecting defects in materials using infrared thermography, in accordance with the method of the present invention. Thermal images of an examination object 1 are obtained via a vacuum chamber 3 by using a thermoplate (thermoelectric module) 2 that utilizes the Peltier effect provided by a semiconductor thermocouple to heat and cool the examination object 1. The Peltier effect thermoplate 2 uses two kinds of thermoelectric semiconductors made respectively of a P-type element and an N-type element and joined by a metallic electrode to form a π-type series circuit. When an N-to-P current flow is set up in the P-N couple, heat is absorbed by the upper part of the circuit and heat is emitted by the lower part. By then pumping heat from the upper part to the lower part, both heating and cooling can be effected.

In the apparatus of FIG. 1, the thermoplate 2 is hermetically attached to one side of the vacuum chamber 3, with the front surface of the thermoplate 2 in contact with the rear surface of the examination object 1 so as to be able to heat and cool the object 1. Thus, a vacuum can be maintained between the examination object 1 and the infrared camera 7, which is arranged with the lens facing a germanium observation window 6. The surface of the examination object is kept in a vacuum to prevent the heat distribution on the surface of the object from being disrupted by the outside atmosphere. The vacuum chamber 3 should be of a suitable size that ensures the examination object 1 is close enough to the infrared camera 7 for accurate measurement while at the same time takes into account the size of the object.

Thermal images obtained with the infrared camera 7 are processed by an image processor 8. For example, microscopic defects can be clarified by subtraction processing of images based on different heating and cooling rates. The thermoplate 2 is connected via a regulator 5 to a temperature controller 4 constituted by a personal computer. Thus, the heating and cooling of the examination object 1 by the thermoplate 2 is automatically controlled by the temperature controller 4 via an RS-232C input/output interface. The examination object 1 is kept in contact with the plate 2 by a load applied by a load device 9.

Figure 2:
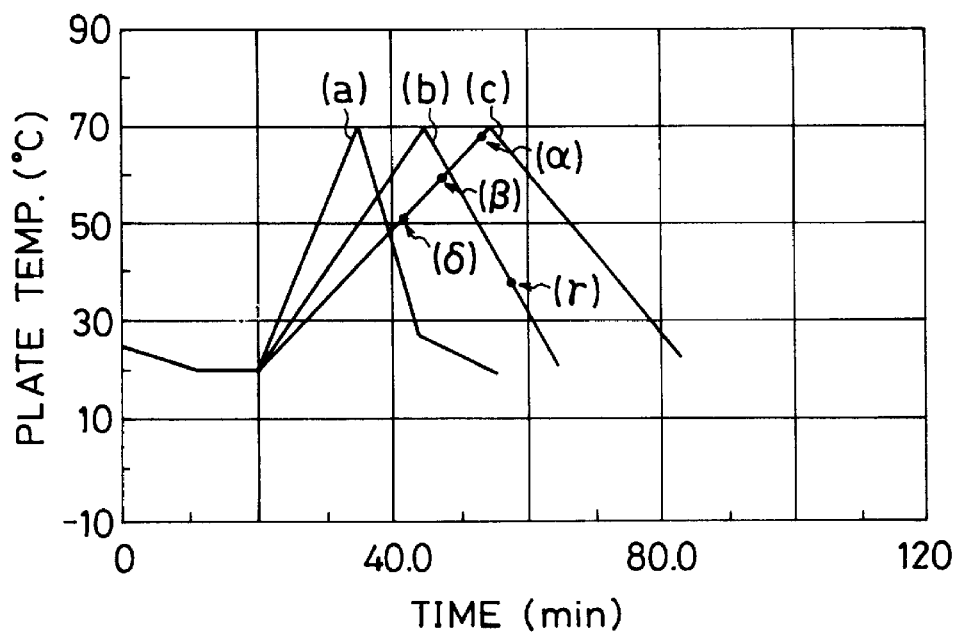
FIG. 2 shows a heating-cooling cycle of the examination object using a thermoplate, in accordance with an embodiment of the method of the invention.

In this apparatus the surface temperature of the examination object 1 can be controlled within the range of from −30° C. to 70° C. at 5 second intervals. As shown in FIG. 2, a desired thermal cycle having set heating and cooling rates can be applied to the examination object 1. To provide precise, stable heating and cooling by the thermoplate 2, a control program was developed for controlling rates of temperature increase and decrease.

When a thermal field is applied to the object for detecting defects using infrared thermography, the object is heated and cooled stably and precisely, during which the temperature distribution on the surface of the object 1 is measured by the infrared camera 7 through the vacuum chamber 3. Thus, the defect detection process can be readily conducted with the disturbing effect of the external air eliminated and the object thus subjected to a thermal field that enables thermal images to be obtained with good reproducibility.

In the following embodiment the method of the present invention is explained with reference to the detection of internal defects in composite laminated sheets of glass fiber-reinforced plastic (GFRP) and in unsaturated polyester resin sheet. However, the invention is not limited to the detection of defects in these materials, but is also applicable to the detection of defects in other composite materials or synthetic resins and in metals and ceramics. The detection of defects based on thermal images can be further enhanced by providing the examination object with a coating of a commercial heat-resistant paint. The thermal images can also be enhanced by using the infrared camera to obtain thermal images of the same object under different conditions, and then using mutual image subtraction processing.

In accordance with an embodiment of the invention, the method of the invention was applied to the detection of internal defects in composite laminated sheets of GFRP and in unsaturated polyester resin, using the apparatus shown in FIG. 1. Details of the results are described below, including a comparison between vacuum and atmospheric conditions, the influence of heating and cooling rates and the effect of painting the samples. Measurements were conducted using a Model 1101 infrared radiation thermometry system made by NEC Sanei Instruments, Ltd. able to measure radiation within the wavelength range of from 8 $\mu$m to 13 $\mu$m, using a HgCdTe detection element and a detector cooled by liquid nitrogen. The frame period was set at 1 second per image. Sample temperature range was −50° C. to 200° C. In this experiment, the minimum detectable temperature difference was 0.1° C.

A 3-mm-thick sample plate, referred to as sample "A", was prepared comprised of three sheets of a GFRP composite material (four-ply glass-reinforced plain weave cloth/unsaturated epoxy resin laminate) measuring 30 mm by 40 mm by 1 mm thick, bonded into a stack using double-sided adhesive tape. The sample had been given man-made defects in the form of three holes drilled in the center sheet, the holes measuring 0.8 mm, 1.5 mm and 3 mm in diameter. A second sample, referred to as sample "B", was fabricated by arranging a strand of carbon fiber (T-300) in a frame, with the fiber stretched lengthwise 2 mm from the bottom of the frame. Polyester resin was then poured into the frame to form a resin plate 4 mm thick, containing defects in the form of voids of various sizes ranging from 0.05 mm to 0.4 mm.

Before examining the samples for defects, the samples were divided into two groups, the samples of one group were given a coating of a black, silicon-based heat-resistant paint, and the samples of the other group were left unpainted. The thermoplate 2 described with reference to FIG. 1 was used to heat and cool the samples, during which a maximum plate temperature of 70° C. was used. For heating and cooling of the samples, the thermoplate 2 was kept in contact with the sample while the regulator 5 was used to control the heating and cooling rates to subject the samples to thermal cycles with various rates of temperature increase and decrease. The vacuum chamber 3 between the sample and the infrared camera 7 was evacuated to the degree of vacuum attainable with a rotary pump, to thereby prevent the temperature distribution on the surface of the sample from being disturbed by the outside air.

An investigation was then conducted to see whether defects, and the size of such defects, could be detected in the samples, by measuring the surface temperature distribution of samples in a vacuum, via the germanium observation window 6. As well as the carbon fiber running lengthwise about 2 mm deep, the 4-mm-thick sample "B" plate also contained defects in the form of voids in the vicinity of the surface and the carbon fiber. For defect detection in a vacuum, sample "B" was arranged in contact with the thermoplate 2 with the voids toward the plate 2, and the infrared camera 7 was used to obtain the surface temperature distribution from the side opposite the plate.

First, the effect of air on thermal images was investigated, using sample "A" having an internal defect, 3 mm in diameter and 1 mm deep. This was done by using the thermoplate 2 to heat and cool the sample in the vacuum chamber 3, and detecting the internal 3 mm defect from temperature distribution measurements taken during the temperature elevation and decrease phases of the thermoplate 2, and comparing these results with measurements taken in air. The results confirmed that the vacuum shut out external disturbances. Curve (a) of FIG. 2 shows the thermal cycle applied in this case.

Figure 3A:
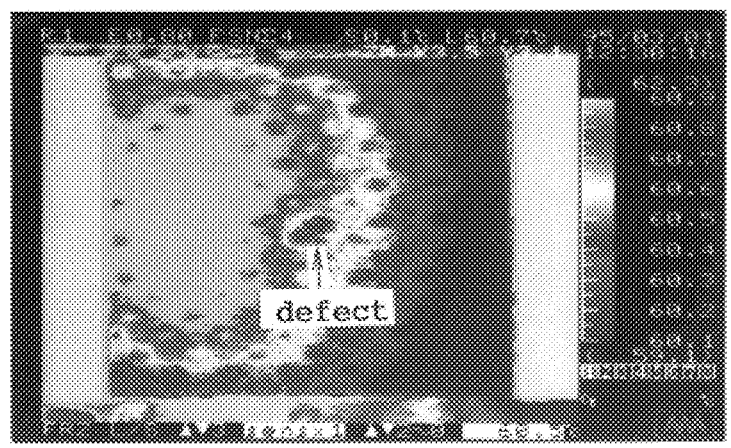
FIG. 3 (A) is a photograph showing a thermogram of a sample "A" structure with a small void, obtained while the sample was being heated in a vacuum.
Figure 3B:
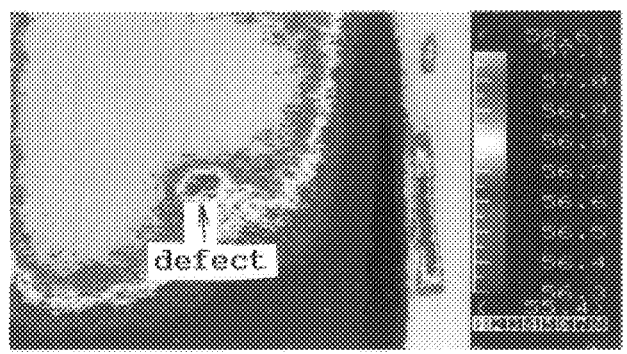

FIG. 3 (A) shows a thermal image obtained while sample "A" was being heated in a vacuum. For comparison, FIG. 3

(B) shows a thermal image obtained while heating a sample "A" in a vacuum chamber in which there was no vacuum. In both cases there was a temperature differential between defects and the surrounding portions, with defect portions being at a lower temperature, enabling the shape of the defects to be confirmed. However, a comparison between thermal images taken in the air and in a vacuum shows that the carbon fiber can be clearly recognized from the thermal image obtained in the vacuum, while clarity is poor in the case of the thermal image obtained in the air. This is because in the air, the temperature distribution is affected by air flows and turbulence to which the sample surface is subject.

Figure 4:
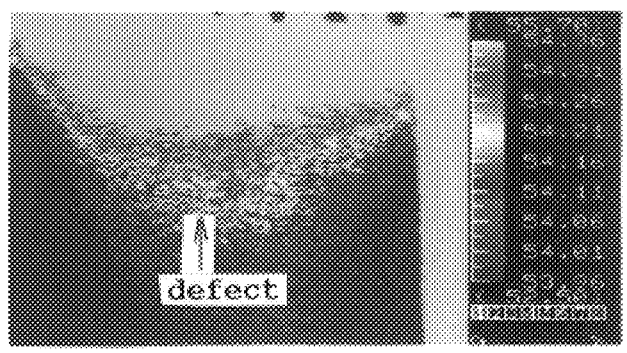
FIG. 4 is a photograph showing a thermogram of the sample "A" structure with a small void, obtained when the sample was subjected to another heating-cooling cycle.
Figure 5:
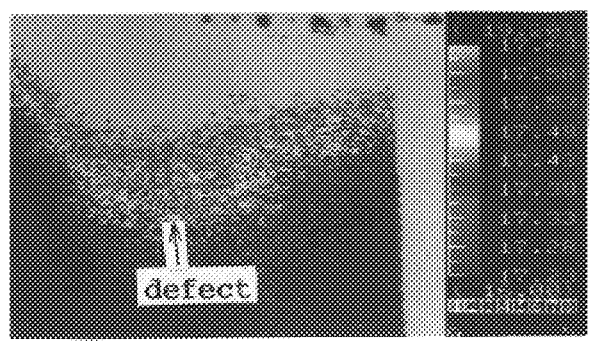
FIG. 5 is a photograph showing a thermogram of a particulate structure with a small void, obtained by image subtraction of two thermal images.

This experiment established the effectiveness of conducting inspections in a vacuum. Next, the effect that different heating and cooling rates by the thermoplate 2 had on the detection of defects in a vacuum was investigated. At the same time, the effectiveness of coating the front and rear surfaces of the sample with black, heat-resistant paint was investigated. The paint was sprayed on. For this experiment, the thermoplate 2 was used to apply heat cycles (a) and (b) of FIG. 2 to a sample "A" having an internal defect in the form of a hole 1.5 mm in diameter. Defect detection was then attempted from thermal images obtained during the heating and cooling phases, but detection was difficult. However, when the sample was heated and cooled using the more gradual temperature gradients of heat cycle (c) of FIG. 2, at point ($\alpha$) at which the thermoplate temperature was about 69° C., within a sample surface temperature of 55° C. to 52° C. a defect portion was detected having a temperature about 0.1° C. higher than the surrounding temperature. The position and size of the defect could be clearly established, as shown in FIG. 4. Subtraction processing of the thermal images was tried as a way of enhancing the outline of the defect. For this, the difference was obtained between a thermal image obtained at point ($\beta$) on the heating gradient of curve (c) of FIG. 2, and a thermal image obtained at point ($\gamma$) on the cooling gradient of curve (b). This made it possible to extract the position and shape of the defect more clearly, as shown in FIG. 5, thereby confirming the efficacy of defect detection by subtraction processing of two thermal images obtained in a vacuum.

Figure 6:
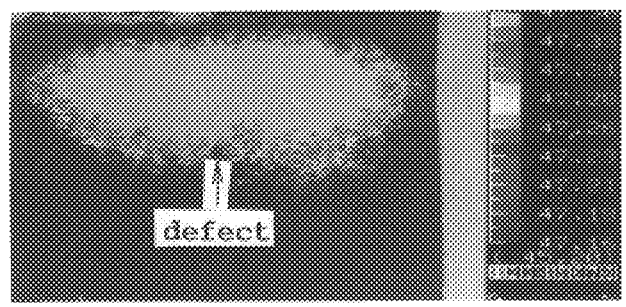
FIG. 6 is a photograph showing a thermogram of a particulate structure with a small void of a sample spray-coated with black paint.

However, subtraction processing did not provide a clearer image of small defects 0.8 mm in diameter. So, a spray coating of black paint was also applied to the surface of the sample "A" on the thermoplate side. Compared to the actual size of the sample, thermal images obtained with this sample were enlarged by 1.38 times along the x axis and 1.6 times along the Y axis. An 0.8 mm defect could not be detected when the thermoplate heating and cooling rates (a) and (b) of FIG. 2 were used. However, in an image taken at point ($\delta$) at a thermoplate temperature of 52° C. on the heating gradient of curve (c), a defect showed up as a region of lower temperature, enabling the position and shape of the defect to be clearly detected, as shown in FIG. 6.

Figure 7:
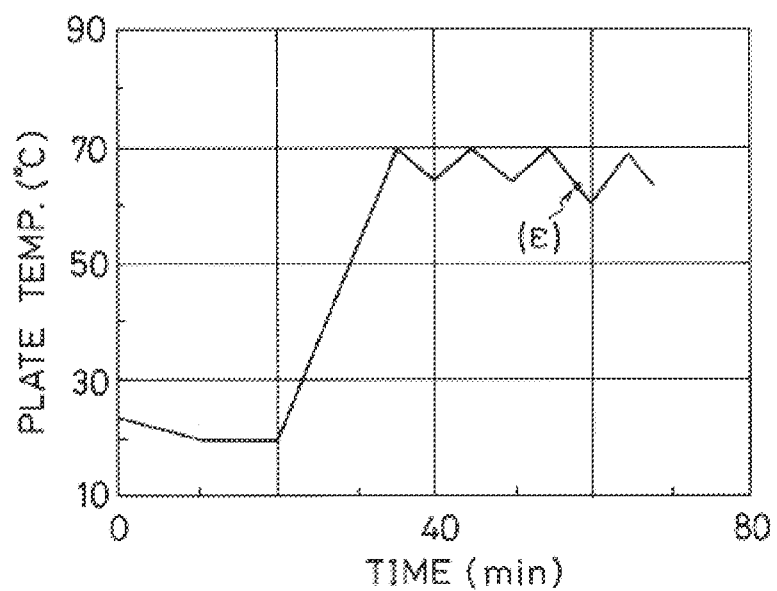
FIG. 7 is a graph showing the course of the thermoplate temperature during a heating-cooling cycle.
Figure 8A:
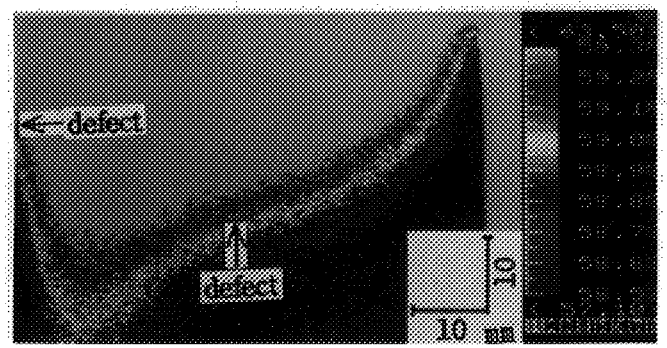
FIG. 8 (A) is a photograph showing an infrared thermogram of a sample particulate structure with small voids, obtained when the sample was subjected to the heating-cooling cycle of FIG. 7.
Figures 8B, 8C:
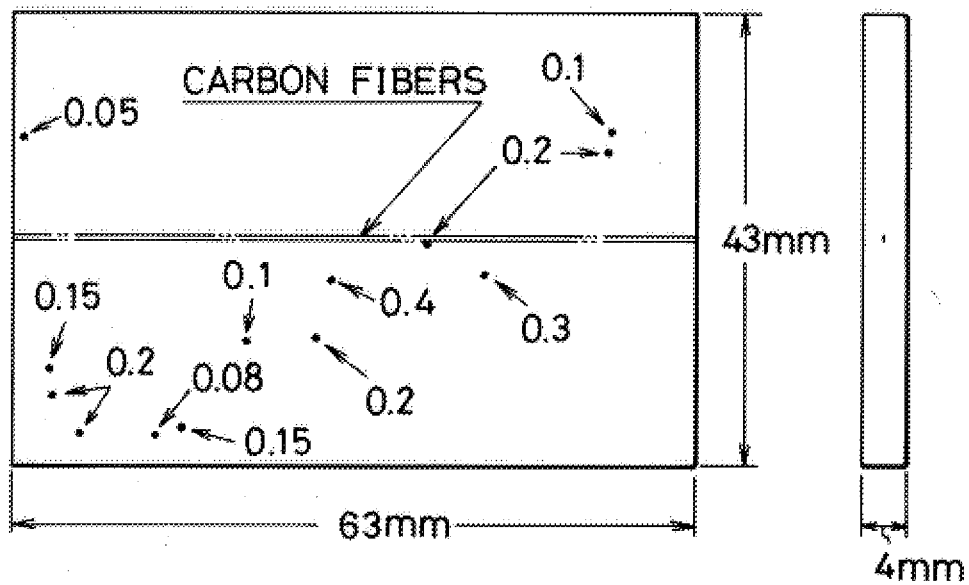

Next, the lower limit to the detection of defects using thermal images obtained from an examination object heated and cooled in a vacuum chamber by a thermoplate was investigated, using sample "B", the unsaturated polyester sample containing voids of various sizes. For this experiment, the surface of the sample on the camera side was given a spray coating of heat-resistant black paint, and the sample was fixed in place with the portion with the voids against the thermoplate. The sample was then repeatedly subjected to the thermal cycle of FIG. 7 to empirically investigate the minimum size defect that can be detected. FIG. 8 (A) shows an infrared thermogram obtained at a thermoplate temperature indicated by ($\epsilon$) on the thermal cycle of FIG. 7. A comparison of the size and position of defects shown in FIG. 8 (A) with the position and size of each defect shown by FIG. 8 (B), which is based on an X-ray view of the same sample taken for confirmation, shows that voids 0.05 mm in diameter are the smallest that can be detected.

As described in the foregoing, the method of detecting defects in materials using infrared thermography according to the present invention, in which a thermoplate is used to heat and cool an examination object in a vacuum to thereby control the thermal field applied to the object, is highly effective for detecting voids and other internal defects of composite materials and the like, enabling, for example, voids as small as 0.05 mm in diameter to be detected within a plate of unsaturated polyester 4 mm thick. Microscopic defects can be detected by subjecting an object to a series of appropriate thermal cycles applied with a thermoplate. Subtraction processing of thermal images obtained with different heating/cooling rates can be used to obtain good effect in the defect detection process. For the detection of defects in GFRP composite materials and the like, it is effective to apply a coating of heat-resistant paint to the object, on the side facing the thermoplate or the side facing the camera.

What is claimed is:

1. A method of detecting defects in materials using infrared thermography, comprising:

placing a rear surface of an examination object close to a front surface of a thermoelectric plate controlled by a temperature controller;

positioning a front surface of the examination object in a vacuum chamber;

disposing an infrared camera outside the vacuum chamber facing the examination object and maintaining a vacuum between the examination object and the infrared camera; and detecting defects in the examination object from thermal images obtained by the infrared camera.

2. The method according to claim 1, wherein said examination object is coated with heat-resistant paint.

3. The method according to claim 2, wherein:

said thermal images of said examination object are obtained under different conditions; and said thermal images are subjected to mutual image subtraction processing.

* * * * *